United States Patent [19]

Long

[11] Patent Number: 4,767,610

[45] Date of Patent: Aug. 30, 1988

[54] METHOD FOR DETECTING ABNORMAL CELL MASSES IN ANIMALS

[75] Inventor: David M. Long, El Cajon, Calif.

[73] Assignee: The Regents of the University of California, Berkeley, Calif.

[21] Appl. No.: 662,728

[22] Filed: Oct. 19, 1984

[51] Int. Cl.$^4$ .............................................. A61K 49/04
[52] U.S. Cl. ........................................................ 424/5
[58] Field of Search ............................................ 424/5

[56] References Cited

U.S. PATENT DOCUMENTS

| | | |
|---|---|---|
| 3,356,575 | 12/1967 | Arbaeus et al. ............................ 424/5 |
| 4,073,879 | 2/1978 | Long ............................................ 424/5 |
| 4,192,859 | 3/1980 | Mackaness et al. ..................... 424/5 |
| 4,285,928 | 8/1981 | Wada et al. ............................... 424/5 |
| 4,490,351 | 12/1984 | Clark ........................................ 424/5 |

FOREIGN PATENT DOCUMENTS 32829  2/1983  Japan ....................................... 424/5

OTHER PUBLICATIONS

Lehninger, Albert L., "Biochemistry: The Molecular Basis of Cell Structure and Function", John Hopkins University School of Medicine, p. 198 (1970).

*Primary Examiner*—Frederick E. Waddell
*Attorney, Agent, or Firm*—Brown, Martin, Haller & Meador

[57] ABSTRACT

An improved method of detecting abnormal cell mass in animals, particularly tumors, wherein a fluorocarbon emulsion and a lysophosphatide or proteinaceous material are administered to animals causing the fluorocarbon to be taken up by the cell mass in hithertofor unobtainable amounts, thus rendering it readily detectable by a variety of physical or chemical methods.

17 Claims, 1 Drawing Sheet

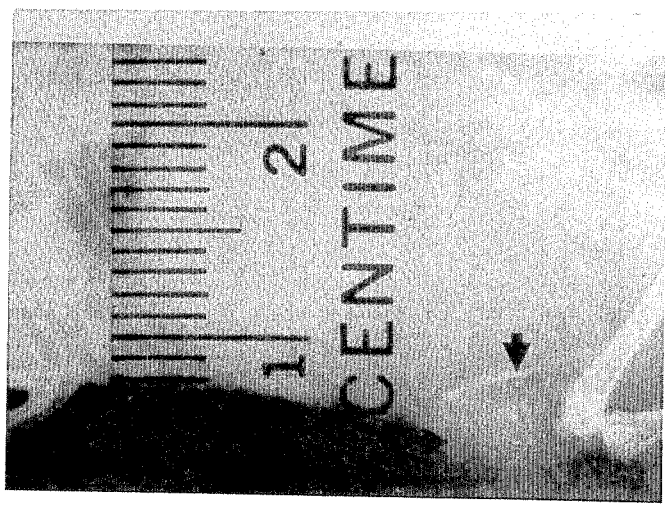
FIG. 1-B
FIG. 1-A

METHOD FOR DETECTING ABNORMAL CELL MASSES IN ANIMALS

This invention was made with Government support under Grant No. CA 32857 awarded by the National Institutes of Health. The Government has certain rights in this invention.

BACKGROUND OF THE INVENTION

This invention relates to an improved method for augmenting the detection of abnormal cell mass in animals utilizing fluorocarbon emulsions.

Medical diagnosis often involves detecting abnormalities in the body using chemicals that differentially contact and/or are taken up by the abnormality thus allowing it to be contrasted from surrounding normal tissues, organs, or bone, as revealed by suitable imaging techniques. To properly image an area of the body, chemical imaging agents must be used and targeted to the desired area. Imaging chemicals fall into four broad categories: those that are radioactive, radiopaque, or paramagnetic, and those that modify acoustic signals. Several factors are considered in choosing a suitable agent—two being the level of sensitivity needed and the imaging method, and the cost and technical problems associated with the use of a particular chemical. Prior work, specifically that of Long and coworkers in *Surgery*, Volume 84, Pages 104–112 (1978) and Aranbulo and coworkers in *Drug Development Communications*, Volume 1, Pages 73–87 (1974), has shown that radiopaque flurocarbons are suitable imaging agents. As taught by Long in U.S. Pat. No. 3,975,512 and U.S. Pat. No. 4,073,879, they are generally administered to an animal as an emulsion consisting of synthetic or naturally occurring emulsifiers, an example of the former being Pluronic F-68 and the latter being lecithin. Moreover, despite the fact that they are less costly to use than radioactive imaging agents, they are nevertheless also quite expensive and possess dose-related side effects. Thus a technique that would increase the imaging-contrast sensitivity and hence decrease the cost of using radiopaque chemicals is highly desirable.

SUMMARY OF INVENTION

The present invention relates to an improved method that unexpectedly enhances the detectability of abnormalities in the body, particularly tumors, premised in increasing the amount of emulsified fluorocarbons that contacts and/or is taken up by the tumor mass. Enhanced uptake of fluorocarbon is effected by the novel method of administering fluorocarbon emulsion with a lysophosphatide or proteinaceous material.

BRIEF DESCRIPTION OF THE DRAWINGS

FIG. 1-A. X-ray of mouse with Colon Tumor-26 in right flank. Mouse received perfluoroctylbromide emulsion without lysolecithin.

FIG. 1-B. X-ray of mouse with Colon Tumor-26 in right flank. Mouse received perfluoroctylbromide emulsion with lysolecithin.

DETAILED DESCRIPTION OF THE INVENTION

The enhanced detection of abnormal cell mass with fluorocarbon is believed to be due to one or more phagocytic cell types that partially compose the mass and that are responsible for taking up most of the fluorocarbon. With regard to tumor detection, the majority of such phagocytic cells are macrophages, which infiltrate the tumor, and in doing so render the tumor mass detectable by a variety of techniques as a result of engulfing and becoming laden with fluorocarbon. The invention brings about the unexpected increase in tumor fluorocarbon content probably in two ways: first, the amount of fluorocarbon taken up per machrophage is increased; and, second, the number of macrophages in the tumor is increased by recruitment to the tumor of either previously existing or newly produced macrophages from throughout the body. In either event, the end result is an increase in the fluorocarbon contact of the tumor mass. Additionally, tumor cells themselves are also phagocytic, although less so than macrophages, and account for some fluorocarbon uptake.

It is anticipated that while the invention is particularly useful for detecting tumors, it can also be used to detect abnormalities such as abscesses and infarcts and normal bodily constituents such as the liver and spleen that consist of, or are infiltrated by, macrophages or are themselves phagocytic.

A fluorocarbon, particularly a radiopaque perfluorocarbon, is emulsified in an aqueous mixture of at least two chemically distinct amphipathic molecules, one chosen from the phosphoglyceride class of lipids and the second from the class of molecules derived from phosphoglycerides and termed lysophosphatides. The latter is a phosphoglyceride derivative minus the fatty acid chain at the 2-position of the glycerol backbone. A phosphoglyceride, lysophosphatide, and fluorocarbon, are combined in a tube and emulsified by one of several techniques, including but not limited to, sonication or passage through a mechanical emulsifier as described by Long et al. in *Surgery*, Volume 84, Pages 104–112 (1978). The final concentration of each is 1%–5%, 0.05%–0.60%, and 10%–50%, respectively. As the concentration of lysophosphatide is increased from 0.05%–0.60%, there is a marked and unexpected increase in the amount of fluorocarbon taken up by the tumor cell mass, as well as an increase in the number of macrophages in the tumor.

Alternatively, fluorocarbons can be emulsified in 1%–5% phosphoglyceride and then administered prior to or simultaneously with proteinaceous material, in lieu of lysophosphatide. Proteinaceous material is a known stimulator of macrophage phagocytic activity and production as described by David and Remington in *Progress in Immunology*, Volume 3, Pages 740–743 (Australian Academy of Science, Canberra 1977). Proteinaceous material, particularly pancreatic protein hormones, cause a dramatic and unexpected increase over the concentration range of 10 μg–1 mg in the amount of fluorocarbon taken up by the tumor mass.

Regardless of whether fluorocarbon is delivered as an emulsion consisting of phosphoglyceride and lysophosphatide, or phosphoglyceride and pancreatic proteins, a single dose of fluorocarbon emulsion, usually 1.5–1.0 g/kg of animal weight, or multiple doses delivered intravenously spaced out over several days is sufficient for fluorocarbon to be taken up and retained by the tumor cell mass. While the fluorocarbon emulsion is generally administered intravenously, other methods of administering it are not excluded, and may even be preferred when the area sought to be imaged is not readily accessible by intravenous injection.

Fluorocarbon-ladened tumor cell mass is capable of being detected for several days after administering the final dose either by X-ray, if the fluorocarbon is radiopaque, or by other techniques such as ultrasound or nuclear-magnetic resonance. Previously unavailable sharp contrast X-ray images of tumors are obtained. The following examples are given to aid in understanding the invention but it is to be understood that the invention is not limited to the particular materials or procedures employed in the examples.

EXAMPLE 1

Effects of Lysolecithin on Colon Tumor 26

FIG. 1 cmpares the X-ray images of a colon tumor in the right flank of mice that received fluorocarbon emulsified with only the phosphoglyceride, lecithin, or with lecithin an the lysophosphatide lysolecithin. The mouse in FIG. 1-A received an emulsion of 20.0% fluorocarbon, specifically perfluoroctylbromide, with 4.0% lecithin as emulsifier and the mouse in FIG. 1-B received twenty percent perfluoroctylbromide with 4.0% lecithin plus 0.6% lysolecithin as the emulsifier. The dose of fluorocarbon was 10 g/kg of animal weight and the mixture was given two days prior to being X-rayed. The emulsion was prepared by sonicating perfluoroctylbromide with lecithin, and with or without lysolecithin as described by Long et al. in *Surgery*, Volume 84, Pages 104-112 (1978). Emulsion was administered intravenously. Note in FIG. 1-A the diffuse, homogenous radiopacity of the tumor as compared to FIG. 1-B. In addition, FIG. 1-B shows not only generalized tumor radiodensity but also radiodense strands (arrows) and rims of increased perfluoroctylbromide (PFOB) concentration. After the animals were exposed to X-ray, the tumors were sized, weighed and the fluorocarbon concentration in the tumors determined by extracting the fluorocarbon and subjecting it to gas chromatography as described by Long et al. in *Surgery*, Volume 84, Pages 104-112 (1978), which consists of extracting the fluorocarbon with isooctane and analysis by gas chromtography with a Packard A7400 gas chromatograph equipped with an electron capture detector with $^{63}$Ni foil. Table I below shows that tumors in mice that received fluorocarbon emulsified with lecithin and varying amounts of lysolecithin exhibit a greater concentration of fluorocarbon when compared to tumors in mice that received fluorocarbon emulsified only in lecithin over the range of 0.1%-0.5% lysolecithin. The increase in the amount of fluorocarbon showed an apparent plateau of 2.5-fold more fluorocarbon in the concentration range of 0.4% -0.5% lysolecithin. Moreover, at the higher lysolecithin concentrations, the tumor mass was reduced.

TABLE I

| | COLON TUMOR 26 | |
|---|---|---|
| Lysolecithin Concentration | Conc. PFOB Experimental: Conc. PFOB Control | Mass Experimental: Mass Control |
| 0.10% | 1.083 | 1.043 |
| 0.20% | 1.070 | 1.527 |
| 0.30% | 1.395 | 1.446 |
| 0.40% | 2.577* | 0.761 |
| 0.50% | 2.569* | 0.347 |

*$p < .01$ when comparing concentration of PFOB mg/gm in tumors from mice receiving PFOB emulsion 10 gm/kg plus lysolecithin in given concentration (Experimental) versus concentration of PFOB in tumors from mice that received PFOB emulsion 10 gm/kg without lysolecithin (Control).

All mice were sacrificed two days after receiving PFOB emulsion. The tumors were excised and weighed and PFOB was extracted and analysed by bas chromatography.

EXAMPLE 2

Effect of Lysolecithin on EMT-6 Tumor

The materials and methods used in this example are identical to those used in Example 1, except that the mice carried a different type of tumor, mammary tumor EMT-6, and an additional lysolecithin concentration, 0.05%, was utilized. Table II below shows that the perfluoroctylbromide emulsified with lysolecithin compared to emulsification without lysolecithin causes a 1.6 to 2.8-fold increase in the fluorocarbon associated with the tumor mass. In addition, at the lysolecithin levels of 0.4%-0.5% there was a decrease in tumor mass.

TABLE II

| | EMT-6 TUMOR | |
|---|---|---|
| Lysolecithin Concentration | Conc. PFOB Experimental: Conc. PFOB Control | Mass Experimental: Mass Control |
| 0.05% | 1.600* | 0.931 |
| 0.10% | 1.906** | 1.088 |
| 0.20% | 1.940** | 1.008 |
| 0.30% | 2.509** | 1.023 |
| 0.40% | 1.866** | 0.880 |
| 0.50% | 2.853** | 0.626* |

*$p < .05$ or **$p < .01$ when comparing concentration of PFOB mg/gm in tumors from mice receiving PFOB emulsion 10 gm/kg plus lysolecithin in the given concentration (Experimental) versus concentration of PFOB in tumors from mice that received PFOB emulsion 10 gm/kg without lyslecithin (Control).

All mice were sacrificed two days after receiving PFOB emulsion. The tumors were excised and weighed and PFOB was extracted and analyzed by gas chromatography.

EXAMPLE 3

Effect of Pancreatic Proteins on Fluorocarbon Uptake by Colon Tumor-26

The materials and methods in this example differ from the others only in that perfluoroctylbromide was emulsified with lecithin only, then the pancreatic hormones, insulin or glucagon, were added in the amounts shown in the table and the mixture injected intravenously into mice. It is apparent from Table III below that both hormones augment the uptake of the fluorocarbon associated with the tumor mass.

TABLE III

| | | COLON TUMOR 26 | |
|---|---|---|---|
| Hormone | Dose | Conc. PFOB Experimental: Conc. PFOB Control | Mass Experimental: Mass Control |
| Insulin | 35 ug | 2.02* | 1.060 |
| Insulin | 70 ug | 2.37* | .738 |
| Glucagon | 20 ug | 1.79* | 1.245 |

*$p < .01$ when comparing concentration of PFOB mg/kg in tumors from mice receiving insulin or glucagon plus PFOB emulsion 10 gm/kg (Experimental) versus concentration of PFOB in tumors from mice that received only PFOB emulsion 10/gm/kg (Control).

All mice were sacrificed two days after receiving PFOB emulsion and the hormone. The tumors were excised and weighted and PFOB was extracted and analyzed by gas chromatography.

I claim:

1. A method for enhancing the detection of tumor cell mass in animals, comprising the steps of:
   forming an emulsion consisting of a radiopaque fluorocarbon at a concentration of about 10-50%, a lysophosphatide, said lysophatide being at a concentration of about 0.05–0.5%, and a phosphoglyceride at a concentration of about 1–5%;

administering said emulsion in an amount sufficient to cause said emulsion to contact said tumor cell mass; and visualizing said tumor cell mass.

2. A method as described in claim 1 wherein said fluorocarbon is radiopaque and is selected from the group consisting of perfluorocarbon and perfluoroctylbromide.

3. A method as described in claim 1 wherein said fluorocarbon is emulsified with phosphatidyl choline phosphoglyceride.

4. A method as described in claim 1 wherein said tumor cell mass is visualized with X-ray, ultrasound, or magnetic resonance.

5. A method for enhancing the detection of tumor cell mass in animals, comprising the steps of:

forming an emulsion of fluorocarbon at a concentration of about 10–50%, said fluorocarbon being radiopaque and selected from the group consisting of perfluorocarbon and perfluoroctylbromide, and a phosphoglyceride at a concentration of about 1–5%, and glucagon;

administering said emulsion to animals in amounts sufficient to cause said emulsion to contact said tumor cell mass; and visualizing said emulsion present in said tumor cell mass.

6. A method as described in claim 5 wherein said phosphoglyceride is phosphatidyl choline.

7. A method as described in claim 5 wherein said glucagon present in said emulsion is administered intravenously to said animals in an effective amount.

8. A method as described in claim 7 wherein said glucagon is administered to animals in one or more amounts of about 10 micrograms to 1 mg/kg of body weight.

9. A composition for distinguishing tumor cell mass from normal tissue, comprising:

a fluorocarbon selected from the group consisting of perfluorocarbon and perfluoroctylbromide, said fluorocarbon being present in about 10–50%;

a lysophosphatide at a concentration of about 0.05–0.5%; and an emulsifier being a phosphoglyceride at a concentration of about 1–5%.

10. A composition as described in claim 9 wherein said phosphoglyceride is phosphatidyl choline.

11. A contrast composition useful for contrasting tumor cell mass from normal tissue, comprising:

a fluorocarbon selected from the group consisting of perfluorocarbon an perfluoroctylbromide, said fluorocarbon being present in an amount of about 10–50%;

glucagon present in an effective amount in said composition; and phosphoglyceride present at a concentration of about 1–5%.

12. A composition as described in claim 11 wherein said phosphoglyceride is phosphatidyl choline.

13. A method for enhancing the detection of tumor cell mass in animals, comprising the steps of:

forming an emulsion of fluorocarbon, said fluorocarbon being at a concentration of about 10–50%, said fluorocarbon being radiopaque and selected from the group consisting of perfluorocarbon and perfluoroctylbromide, and a phosphoglyceride at a concentration of about 1–5%, and insulin;

administering said emulsion to animals in amounts sufficient to cause said emulsion to contract said tumor cell mass and;

visualizing said emulsion present in said tumor cell mass.

14. A method as described in claim 13 wherein said insulin present in said emulsion is administered intravenously to said animals in an effective amount.

15. A method as described in claim 14 wherein said insulin is administered to animals in one or more amounts of about 10 micrograms to 1 mg/kg of body weight.

16. A contrast composition useful for contrasting tumor cell mass from normal tissue patients, comprising:

a fluorocarbon selected from the group consiting of perfluorocarbon and perfluoroctylbromide, said fluorocarbon being radiopaque and present at a concentration of about 10–50%;

insulin at a concentration of about 10 micrograms-1 mg per kilogram of patient body weight; and a phosphoglyceride at a concentration of about 1–5%.

17. A composition as described in claim 16 wherein said phosphoglyceride is phosphatidyl choline.

* * * * *

UNITED STATES PATENT AND TRADEMARK OFFICE
CERTIFICATE OF CORRECTION

PATENT NO. : 4,767,610

DATED : August 30, 1988

INVENTOR(S) : David M. Long

It is certified that error appears in the above-identified patent and that said Letters Patent is hereby corrected as shown below:

Column 6, claim 13, line 24 "contract" should be --contact--

Signed and Sealed this

Thirteenth Day of June, 1989

*Attest:*

DONALD J. QUIGG

*Attesting Officer*   Commissioner of Patents and Trademarks